United States Patent
Zhang et al.

(10) Patent No.: US 9,983,159 B2
(45) Date of Patent: May 29, 2018

(54) DETECTING DELAMINATION IN A COMPOSITE COMPONENT

(71) Applicant: ROLLS-ROYCE PLC, London (GB)

(72) Inventors: Bing Zhang, Bristol (GB); Giuliano Allegri, London (GB)

(73) Assignee: ROLLS-ROYCE plc, London (GB)

( * ) Notice: Subject to any disclaimer, the term of this patent is extended or adjusted under 35 U.S.C. 154(b) by 145 days.

(21) Appl. No.: 14/848,996

(22) Filed: Sep. 9, 2015

(65) Prior Publication Data

US 2016/0103087 A1   Apr. 14, 2016

(30) Foreign Application Priority Data

Oct. 8, 2014  (GB) .................................. 1417781.0

(51) Int. Cl.
| | |
|---|---|
| *G01N 27/20* | (2006.01) |
| *F01D 5/28* | (2006.01) |
| *G01M 15/14* | (2006.01) |
| *G01N 27/24* | (2006.01) |

(52) U.S. Cl.
CPC ............. *G01N 27/20* (2013.01); *F01D 5/282* (2013.01); *G01M 15/14* (2013.01); *G01N 27/24* (2013.01); *Y02T 50/672* (2013.01)

(58) Field of Classification Search
CPC ................................ G01N 27/20; G01N 27/24
USPC ................................................ 324/71.1–71.6
See application file for complete search history.

(56) References Cited

U.S. PATENT DOCUMENTS

| | | | |
|---|---|---|---|
| 4,674,334 A | 6/1987 | Chimenti et al. | |
| 4,972,018 A * | 11/1990 | Leadbetter | C09J 103/02 156/328 |
| 6,313,646 B1 * | 11/2001 | Davis | G01N 17/02 204/404 |
| 6,370,964 B1 * | 4/2002 | Chang | G01B 5/30 73/862.046 |
| 2003/0106376 A1 | 6/2003 | Shirzad et al. | |
| 2008/0034881 A1 * | 2/2008 | Haase | G01L 1/2287 73/768 |
| 2009/0294022 A1 | 12/2009 | Hayes et al. | |

(Continued)

FOREIGN PATENT DOCUMENTS

| | | |
|---|---|---|
| GB | 2 381 670 A | 5/2003 |
| GB | 2 479 776 A | 10/2011 |
| GB | 2 482 588 A | 2/2012 |

OTHER PUBLICATIONS

Feb. 24, 2016 Search Report issued in European Patent Application No. 15184461.

(Continued)

*Primary Examiner* — Jeff Natalini
(74) *Attorney, Agent, or Firm* — Oliff PLC

(57) ABSTRACT

A method of detecting delamination of a composite component, the composite component having a plurality of plies and a plurality of z-pins extending through the composite component in a direction transverse to the plies. The method includes measuring one or more material properties of one or more of the z-pins. The measured material properties are compared to reference material properties. An estimation of whether delamination has occurred is performed based upon the comparison of the measured material properties and the reference material properties.

14 Claims, 7 Drawing Sheets

(56) References Cited

U.S. PATENT DOCUMENTS

2011/0122591 A1   5/2011   Hucker et al.

OTHER PUBLICATIONS

Hou L. et al. "Technical Note; A resistance-based damage location sensor for carbon-fibre composites", Smart Materials and Structures, IOP Publishing Ltd., Bristol, GB, vol. 11, No. 6, Nov. 4, 2002, pp. 966-969.

Jan. 23, 2015 Search Report issued in British Patent Application No. GB1417781.0.

* cited by examiner

DETECTING DELAMINATION IN A COMPOSITE COMPONENT

FIELD OF INVENTION

The present invention relates to a method of detecting delamination in a composite component, a system for use in detecting delamination in a composite component, a composite component arrangement, and/or a gas turbine engine.

BACKGROUND

Gas turbine engines are typically employed to power aircraft. Typically a gas turbine engine will comprise an axial fan driven by an engine core. The engine core is generally made up of one or more turbines which drive respective compressors via coaxial shafts. The fan is usually driven directly off an additional lower pressure turbine in the engine core.

The fan comprises an array of radially extending fan blades mounted on a rotor and will usually provide, in current high bypass gas turbine engines, around seventy-five percent of the overall thrust generated by the gas turbine engine. The remaining portion of air from the fan is ingested by the engine core and is further compressed, combusted, accelerated and exhausted through a nozzle. The engine core exhaust mixes with the remaining portion of relatively high-volume, low-velocity air bypassing the engine core.

The fan blades and/or a casing that surrounds the fan may be manufactured from metallic and/or composite non-metallic materials. Generally fan blades include a composite body and a metallic leading edge and tip.

Composite components are often laminate structures that include a plurality of plies. Each ply generally includes a reinforcing fibres (e.g. high strength or high stiffness fibres) embedded in a matrix, e.g. a plastic matrix material. The matrix material of adjacent stacked plies is bonded together to build the composite component. The matrix material is weaker than the fibre material and as such the bond between stacked plies can form a point of weakness. This means that a primary failure mechanism of concern for composite materials is delamination.

Delamination for example of a fan blade may occur in the event of an impact by a foreign object such as a bird strike.

To reduce the risk of delamination of a composite component through thickness reinforcement can be used. One type of through thickness reinforcement is z-pinning. A component that has been z-pinned includes a plurality of rods (known as z-pins) extending through the thickness of the component in a direction transverse to the general direction of the plies. Z-pins are generally made of a metallic or composite material and typically have a diameter ranging from or equal to approximately 0.3 mm to 0.5 mm. Often, composite z-pins are manufactured by pultrusion of a carbon fibre tow impregnated by a thermoset resin. The z-pins of a composite component exert a bridging force on the plies to hold the plies in position relative to each other, this reduces opening of inter-laminar cracks (known as mode I failure) and sliding displacements of inter-laminar cracks (known as mode II failure).

Although the z-pins can substantially arrest crack propagation, it is often not possible to eliminate crack propagation in a composite component. Accordingly, it would be useful to detect when delamination has occurred, and the extent and/or location of such delamination so as to indicate when a component needs repair or replacement.

SUMMARY OF INVENTION

A first aspect of the disclosure provides a method of detecting delamination of a composite component, the composite component having a plurality of plies and a plurality of z-pins extending through the composite component in a direction transverse to the plies (e.g. in a through-thickness direction). The method comprises measuring one or more material (or physical) properties of one or more of the z-pins. The measured material properties are compared to reference material properties. An estimation of whether delamination has occurred is based upon the comparison of the measured material properties and the reference material properties.

The method may comprise the step of estimating an expected extent of any delamination that has occurred.

The method may comprise comparing the one or more detected material properties to an expected material property for a composite component without any delamination.

The method may comprise comparing one or more detected material properties to one or more expected material properties for a composite component at one or more stages of delamination.

The method may comprise measuring one or more material properties of a plurality of z-pins.

The method may comprise estimating the expected location of delamination based upon the comparison of the detected material properties for the z-pins with the reference material properties.

The material properties of a plurality or a series of z-pins may be measured sequentially.

The method may comprise comparing the one or more detected material properties to an expected material property for a composite component without any delamination.

The method may comprise comparing one or more detected material properties to one or more expected material properties for a composite component at one or more stages of delamination.

The material properties detected may be electrical properties. For example, resistance, potential, current, charge and/or capacity may be measured. Additionally or alternatively, the material properties detected may include thermo-electric properties or ultrasonic properties.

One or more electrodes may be connected to one or more of the z-pins of the composite component. For example, the electrodes may be connected to each longitudinal end of the z-pins to form an electrode pair. The electrical properties of the z-pins may be measured across the z-pin, e.g. resistance may be the resistance experienced by an electrical signal passing from one electrode at one end of the z-pin to the other electrode at the opposite longitudinal end of the z-pin.

One electrode may connect between multiple z-pins.

The z-pins may protrude from the composite component. The electrodes may be connected to a protruding end of the z-pins.

Each electrode may comprise a conductive material provided on the surface of the component or embedded in the component, and in contact with one or more z-pins. For example, the z-pins may not protrude from an external surface of the composite component and the conductive material may be provided to connect the non-protruding z-pins to the electrodes.

The method may include applying a conductive material to a surface or ply layer of the component. The conductive material may be applied using sputtering or printing with conductive ink.

The method may comprise co-curing the electrodes with the composite component. Alternatively, the method may comprise bonding the electrodes to a surface of the composite component (i.e. a surface transverse to the principal or longitudinal axis of the z-pins).

The composite component may comprise a protective coating or layer. The protective coating or layer may cover protruding z-pins and or electrodes provided on the surface of the component. The protective coating or layer may be an elastomeric paint or a metallic shim. In the case of a metallic shim, the electrodes and/or protruding ends of the z-pins may be insulated e.g. covered or at least partially by an insulating material (e.g. embedded in a plastic material).

The method may comprise transmitting a signal indicative of the material properties of one or more z-pins to a measurement unit where the signal is converted to one or more material property measurements. The method may comprise transmitting data related to the one or more material property measurements to a data acquisition unit where the measured material properties are recorded. The method may comprise transmitting the recorded material properties to a data analyser where the measured properties are compared to reference material properties.

The composite component may be a component of a gas turbine engine, e.g. a fan blade or casing.

A second aspect of the disclosure provides a system for detecting delamination of a composite component having z-pins. The system comprises one or more measurement arrangements configured to measure material (or physical) properties of one or more z-pins of a composite component. A data processing unit is provided.

The data processing unit is configured to: receive a signal from the one or more measurement arrangements; compare data from the signal to one or more reference parameters; and estimate whether delamination of the composite component has occurred based upon the comparison of data from the signal to one or more reference parameters.

The system may be used to implement the method of the first aspect. Accordingly, the system may be configured to perform the method of the first aspect and one or more of the optional features of the method of the first aspect.

The measurement arrangement may comprise one or more electrodes connectable to be in electrical communication with one or more z-pins.

The measurement arrangement may comprise one or more measurement channels. For example, the measurement arrangement may comprise one or more electrode pairs.

The data processing unit may comprise a measurement unit configured to receive a signal from the one or more measurement arrangements.

The data processing unit may comprise a data acquisition unit configured to record data from a signal from the one or more measurement arrangements.

The data processing unit may comprise a data analyser configured to compare to the signal to reference data. For example, the data analyser may be configured to compare data associated with a signal received from the one or more measurement arrangements to corresponding expected data for a composite component without any delamination. Additionally or alternatively, the data analyser may be configured to compare data associated with a signal received from the one or more measurement arrangements to corresponding expected data for a composite component at one or more stages of delamination.

The system may comprise a control unit configured to control when the data processing unit should receive and/or process a signal from the one or more measurement arrangements.

The system may comprise a plurality of measurement arrangements and wherein the control unit is configured to receive sequential measurements from each of the measurement arrangements. For example, the system may comprise a plurality of electrode pairs and the control unit may be configured to receive sequential measurements from each of the electrode pairs.

The system may comprise a switch module operable to control when a signal is transmitted to the data processing unit from a given measurement arrangement.

A third aspect of the disclosure provides a system for detecting delamination of a composite component having z-pins. The system comprises one or more electrodes connectable to one or more z-pins of a composite component. A data processing unit is provided. The data processing unit is configured to: receive an electrical signal from the one or more electrodes; compare data from the signal to one or more reference parameters; and estimate whether delamination of the composite component has occurred based upon the comparison of data from the signal to one or more reference parameters.

The system of the third aspect may be used to implement the method of the first aspect. Accordingly, the system of the third aspect may be configured to perform the method of the first aspect and one or more of the optional features of the method of the first aspect. It will be understood to the person skilled in the art that the system of the third aspect may have one or more of the optional features of the system of the second aspect.

A fourth aspect of the disclosure provides a composite component arrangement comprising the system according to the second aspect and a composite component. The composite component has a plurality of plies and a plurality of z-pins extending through the composite component in a direction transverse to the plies (e.g. in a through thickness direction). One or more measurement arrangements of the system are connected to one or more z-pins of the composite component.

The z-pins may protrude from an external surface of the composite component plies.

The one or more measurement arrangements may comprise electrodes having conductive material provided on a surface of the composite component (e.g. an external-most ply of the composite component). The one or more measurement arrangements may comprise electrodes having conductive material provided on a surface of a ply of the composite component (e.g. embedded in the composite component).

The conductive material may connect a plurality of z-pins.

A protective coating or layer may be provided on an outer surface of the composite component and the z-pins and/or electrodes may be protected by said protective coating or layer.

The protective coating or layer may be an elastomeric paint or a metal shim. In the case of a metal shim, the electrodes and/or ends of the z-pins may be embedded in an insulating material such as plastic.

The one or more measurement arrangements may be connected to the composite component during the process of curing the composite.

The one or more measurement arrangements may be bonded to the surface of the composite component, e.g. using adhesive.

A single measurement arrangement may measure material properties of multiple z-pins.

The z-pins may be carbon fibre z-pins and the measurement arrangement may be configured to measure potential or resistance. The z-pins may be metallic and the measurement arrangement may be configured to measure potential or resistance.

A fifth aspect of the disclosure provides a gas turbine engine comprising the system according to the second or third aspect and/or the arrangement according to the fourth aspect.

DESCRIPTION OF DRAWINGS

The invention will now be described, by way of example only, with reference to the accompanying drawings in which.

DETAILED DESCRIPTION

Figure 1:
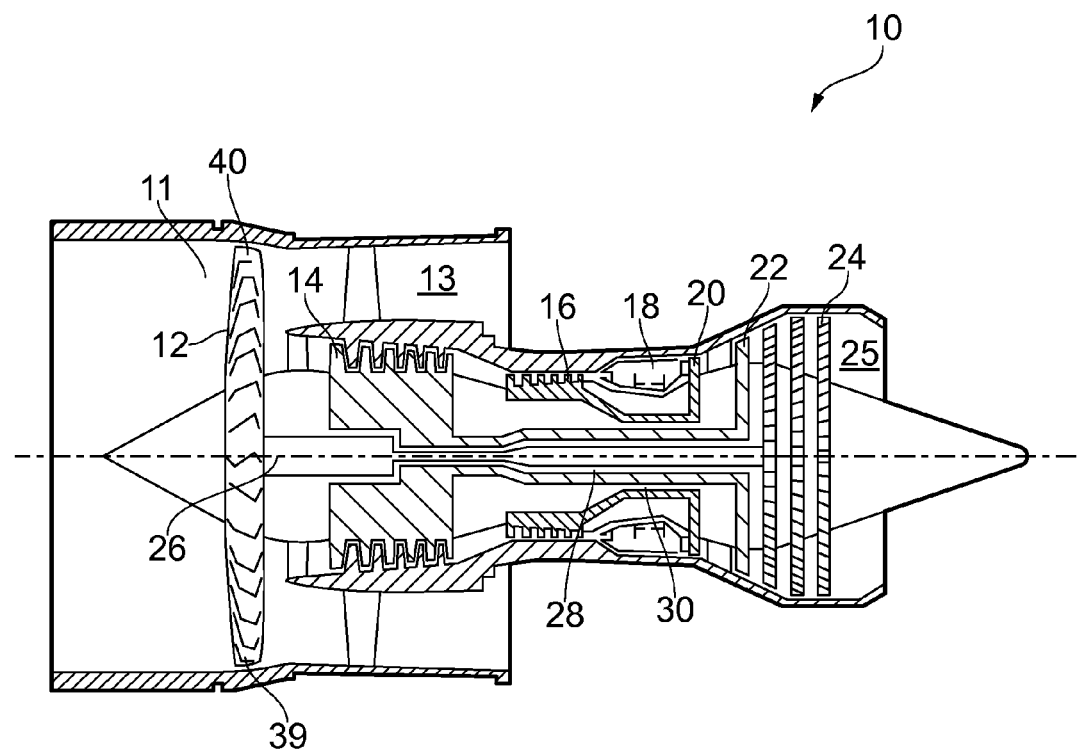
FIG. 1 illustrates a cross section of a gas turbine engine.

With reference to FIG. 1 a bypass gas turbine engine is indicated at 10. The engine 10 comprises, in axial flow series, an air intake duct 11, fan 12, a bypass duct 13, an intermediate pressure compressor 14, a high pressure compressor 16, a combustor 18, a high pressure turbine 20, an intermediate pressure turbine 22, a low pressure turbine 24 and an exhaust nozzle 25. The fan 12, compressors 14, 16 and turbines 20, 22, 24 all rotate about the major axis of the gas turbine engine 10 and so define the axial direction of the gas turbine engine.

Air is drawn through the air intake duct 11 by the fan 12 where it is accelerated. A significant portion of the airflow is discharged through the bypass duct 13 generating a corresponding portion of the engine thrust. The remainder is drawn through the intermediate pressure compressor 14 into what is termed the core of the engine 10 where the air is compressed. A further stage of compression takes place in the high pressure compressor 16 before the air is mixed with fuel and burned in the combustor 18. The resulting hot working fluid is discharged through the high pressure turbine 20, the intermediate pressure turbine 22 and the low pressure turbine 24 in series where work is extracted from the working fluid. The work extracted drives the intake fan 12, the intermediate pressure compressor 14 and the high pressure compressor 16 via shafts 26, 28, 30. The working fluid, which has reduced in pressure and temperature, is then expelled through the exhaust nozzle 25 generating the remainder of the engine thrust.

The intake fan 12 comprises an array of radially extending fan blades 40 that are mounted to the shaft 26. The shaft 26 may be considered a hub at the position where the fan blades 40 are mounted. The fan blades are surrounded by a fan casing 39, which may be made from a composite material.

Figure 2:
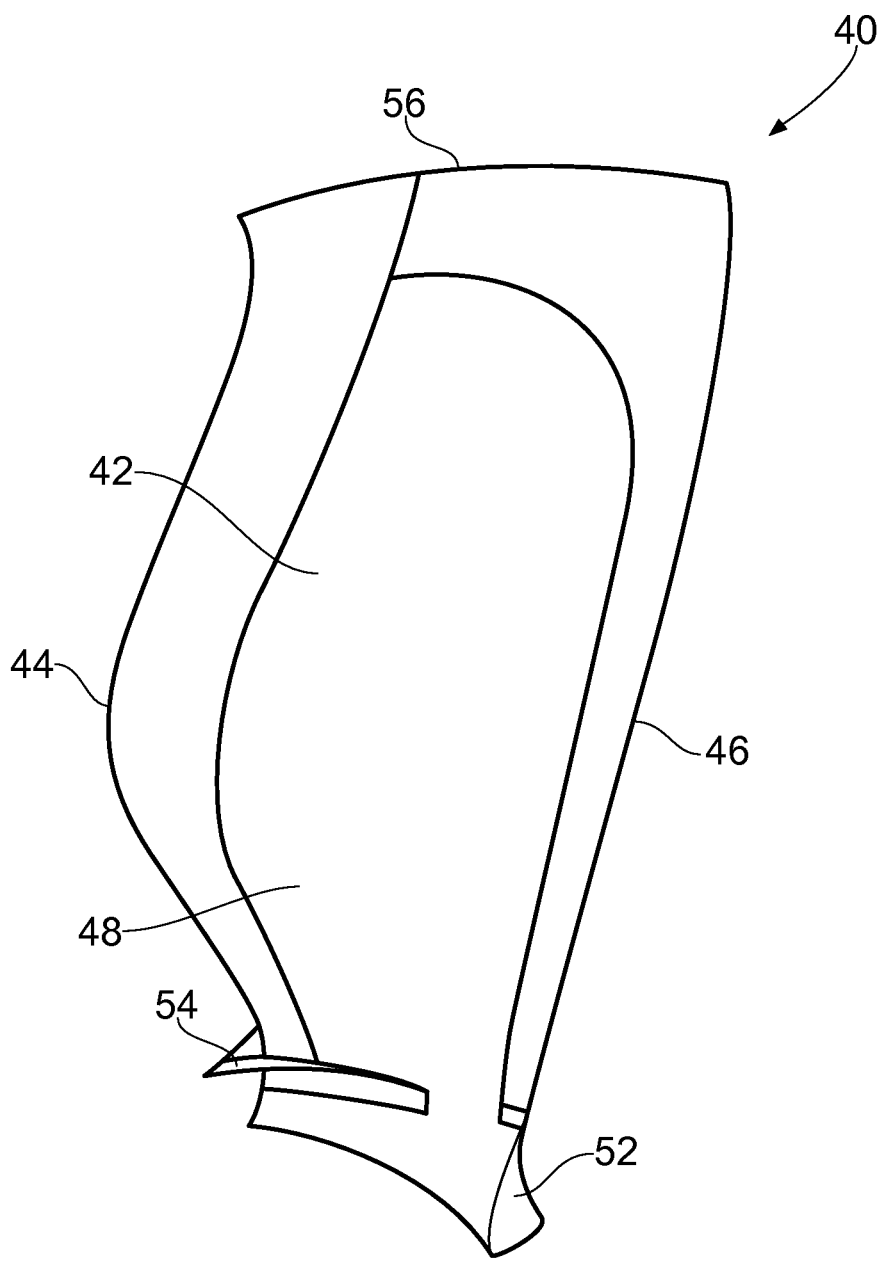
FIG. 2 illustrates a composite fan blade.

Referring to FIG. 2, the fan blades 40 each comprise an aerofoil portion 42 having a leading edge 44, a trailing edge 46, a concave pressure surface wall 48 extending from the leading edge to the trailing edge and a convex suction surface wall extending from the leading edge to the trailing edge. The fan blade has a root 52 via which the blade can be connected to the hub. The fan blade has a tip 56 at an opposing end to the root. The fan blade may also have an integral platform 54 which may be hollow or ribbed for out of plane bending stiffness. The fan blade includes a metallic leading edge and a metallic tip and the remainder of the fan blade is made from composite material.

The composite fan blade 40 and/or the composite casing 39 may be reinforced using rods (known as z-pins) that extend through the thickness of the blade or casing.

It will be understood by the person skilled in the art that the following discussion relates generally to composite components, but in exemplary embodiments the composite component may be a fan blade or a fan casing.

Figure 3:
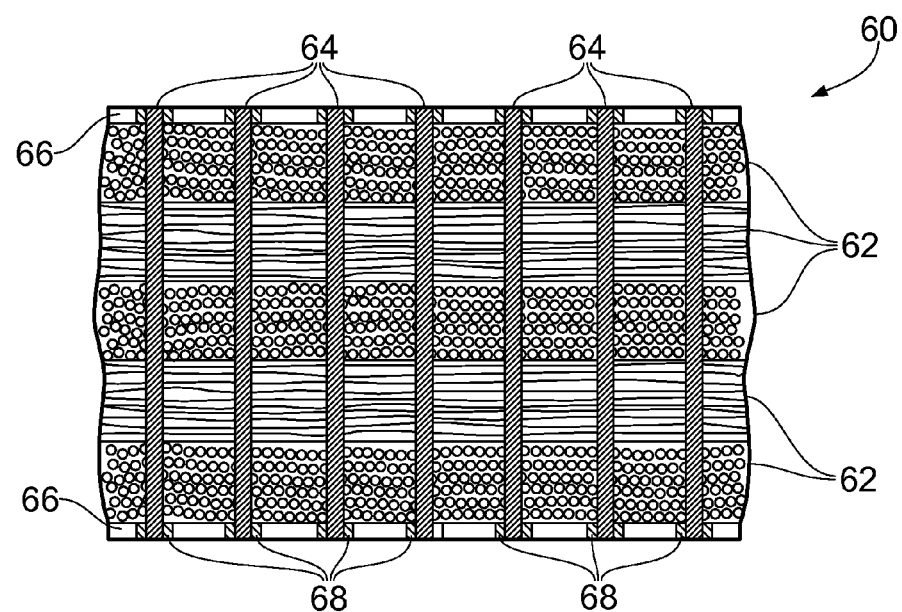
FIG. 3 illustrates a cross section of a composite component that is reinforced using z-pins.

Referring to FIG. 3, a composite component is indicated generally at 60. The composite component 60 includes a plurality of stacked fibre reinforced plies 62. Neighbouring stacked plies are arranged to be angled to each other, e.g. transverse to each other, and using terminology of the art would be referred to as having different orientations. Z-pins 64 extend through the thickness of the component 60. In the present embodiment the z-pins are carbon fibre z-pins, but as will be understood by the person skilled in the art the z-pins could be made from any suitable material (e.g. metallic (such as titanium).

The boundary between each stacked ply (e.g. the boundary between the plies in a through-thickness direction of the composite, or a vertical direction in the orientation shown in FIG. 3) can be a fault plane along which the composite component 60 can delaminate. The principle modes of delamination of concern are mode I (i.e. crack opening—e.g. one of the plies separating from an adjacent ply in through-thickness direction or a vertical direction in the orientation shown in FIG. 3) and mode II (i.e. one of the plies sliding relative to an adjacent ply). The z-pins 64 are provided to reinforce the composite component 60 and extend through each of the plies 62 of the component 60. The present inventors have recognised that during delamination the material properties of the z-pins are altered, and this change in material properties can be used to detect and/or locate delamination. During mode I delamination, the z-pins may be progressively pulled out of the laminate and during mode II delamination, the z-pins may be ruptured by shear.

In exemplary embodiments, ultrasound or thermoelectric properties may be used to indicate delamination, but the following examples will concentrate on using a change in electrical properties to detect and/or locate delamination. The measured electrical properties may be resistance, potential, charge, capacity and/or current. The most appropriate measurement may depend upon the material of the z-pin. For example, if the z-pins are made from carbon or metal the potential or resistance of the pin may be measured.

As will now be explained, to measure the material (or physical) properties of the z-pins a measurement arrangement can be provided in communication with the z-pins and a data processing system can be provided to process and analyse signals from the measurement arrangement. In the following examples where the measured properties are electrical properties, the measurement arrangement comprises electrodes.

Referring again to the embodiment shown in FIG. 3, the z-pins 64 protrude from the outer surfaces of the external most plies 62. Electrodes 68 can be connected to the protruding portion of the z-pins. One electrode may be connected to one longitudinal end of a z-pin (the upper protruding end in the orientation shown in FIG. 3) and another electrode may be connected to an opposite longitudinal end of the z-pin (e.g. the lower protruding end in the orientation shown in FIG. 3), said electrodes can be considered to form an electrode pair. One or more protective layers (or coatings) 66 may be applied to the outer surfaces of the composite component 60. In this case, each protective layer is provided on the same surface as the electrodes and the protruding portion of the z-pins. The protective layer could be an elastomeric paint or a metal shim. In the case of the metal shim the electrodes and/or the protruding portion of the z-pins may be insulated from the protective layer through an insulating material, for example a plastic material, to avoid short circuiting. The electrodes may be co-cured with the composite component during the manufacturing process or the electrodes may be bonded (e.g. using adhesive) to the composite component after the cure of the composite.

Figure 4:
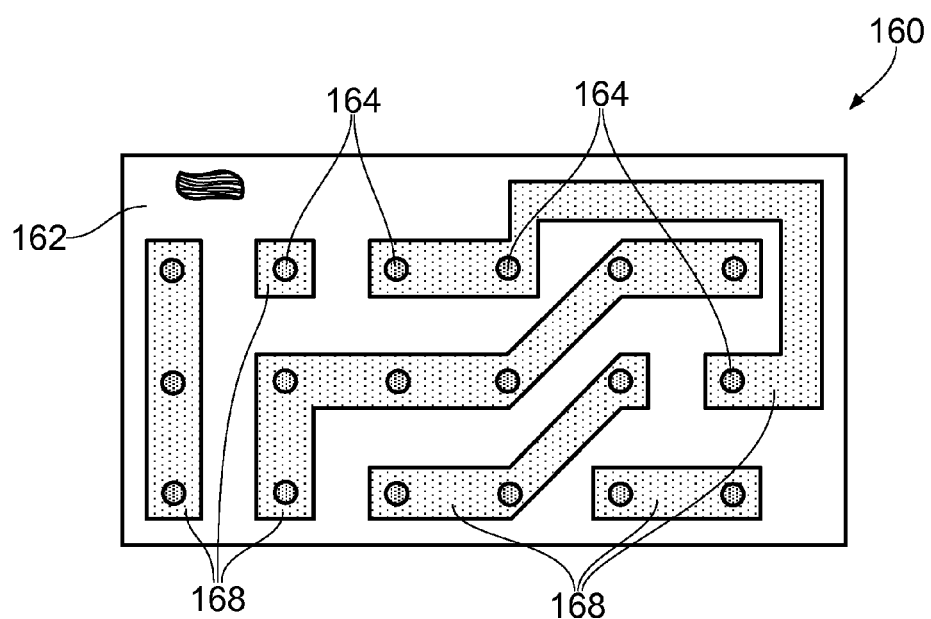
FIG. 4 illustrates a plan view of an outer surface of an alternative composite component having an electrode array.

An alternative composite component is indicated at 160 in FIG. 4. The electrodes 168 of the composite component 160 are provided as films of conductive material deposited on the external surface of the composite component 160. The z-pins 164 of the composite component 160 are flush to the conductive material deposited on the surface of the stack of plies instead of protruding from the surface of the composite component. The film of conductive material may be provided by sputtering or printing with conductive ink. As can be seen in FIG. 4, some of the electrodes 168 connect to only a single z-pin, but some of the electrodes connect to a plurality of z-pins (e.g. two, three, or six z-pins). In the described arrangement on electrode pair forms one measurement channel. When a component is large, e.g. a fan blade, connecting one measurement channel to multiple z-pins can reduce the complexity of the measurement arrangement. When one measurement channel is connected to multiple z-pins, the collective properties of a plurality of z-pins or the properties of individual z-pins may be measured.

In a further alternative embodiment not illustrated, the electrodes may be embedded within the composite component, for example films of conductive material may be provided on one or more internal plies of the composite component.

Figure 5:
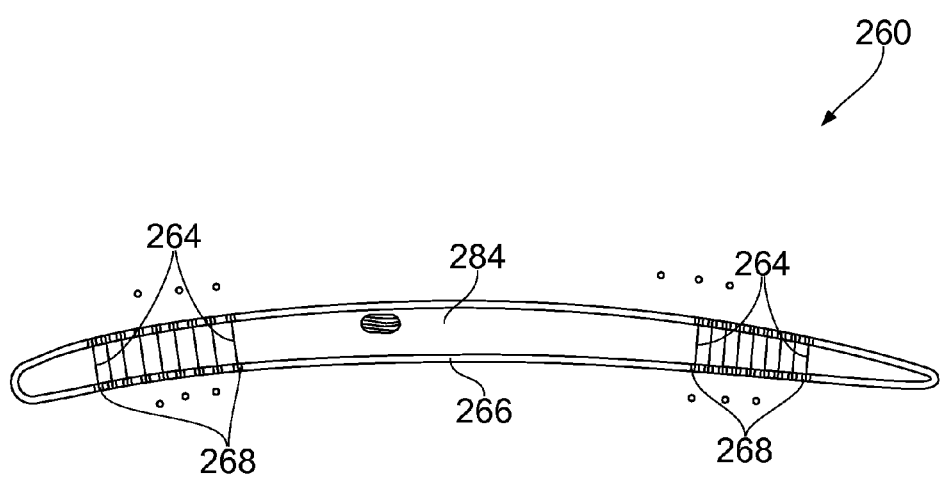
FIG. 5 illustrates a cross-section of a composite component having z-pins.

A yet further alternative composite component is indicated generally at 260 in FIG. 5. The plies (or laminates) of the composite component 260 form a tapered and curved body 284. Z-pins 264 extend through the thickness of the body 284. Electrodes 268 are embedded into an outer protective layer 266, which may be an elastomeric film or a metal shim. When protective layer is a metal shim, the electrodes are electrically insulated e.g. with a plastics material.

Figure 6:
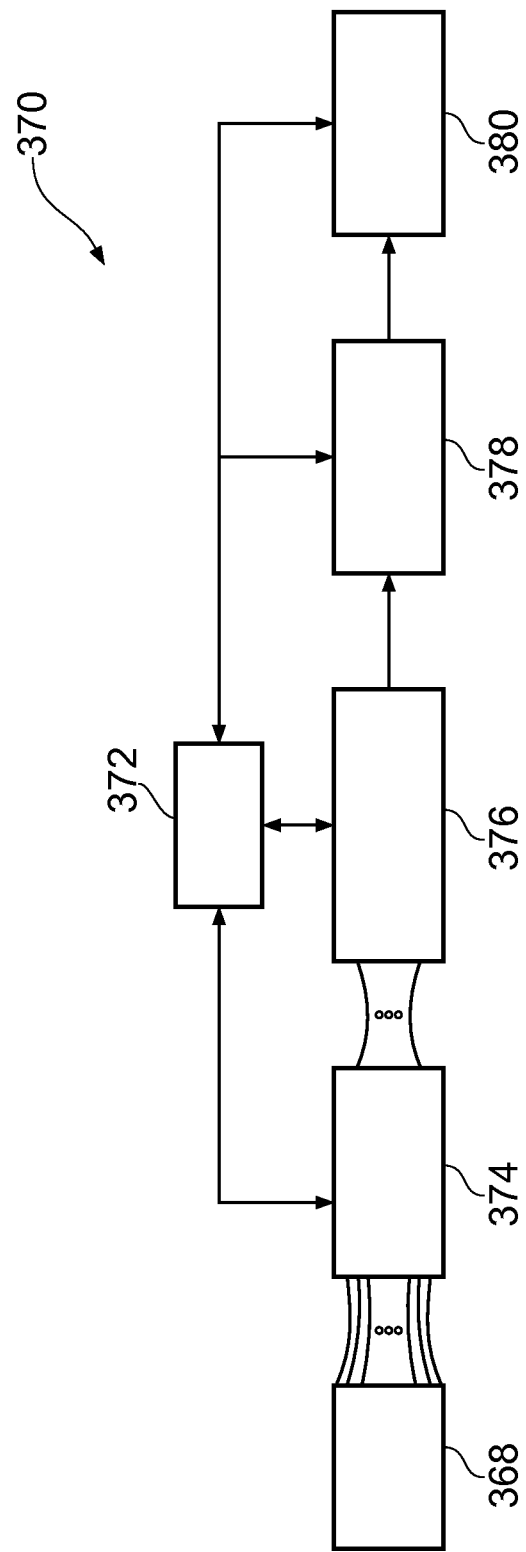
FIG. 6 illustrates a signal detection system for detecting delamination of the composite component of FIG. 3, 4 or 5.

Referring now to FIG. 6, a system 370 is provided for detecting delamination of a composite component such as the composite components 60, 160 and 260 shown in FIGS. 3, 4 and 5.

The system 370 includes a control unit 372, a switch module 374, a measurement unit 376, a data acquisition unit 378 and a data analyser 380.

The control unit 372 may comprise any suitable circuitry to cause performance of the methods described herein. The control unit 372 may comprise: at least one application specific integrated circuit (ASIC); and/or at least one field programmable gate array (FPGA); and/or single or multi-processor architectures; and/or sequential (Von Neumann)/parallel architectures; and/or at least one programmable logic controllers (PLCs); and/or at least one microprocessor; and/or at least one microcontroller, to perform the methods.

By way of an example, the control unit 372 may comprise at least one processor and at least one memory. The memory may store a computer program comprising computer readable instructions that, when read by the processor, causes performance of the methods described herein. The computer program may be software or firmware, or may be a combination of software and firmware.

The processor may be located on the gas turbine engine 10, or may be located remote from the gas turbine engine 10, or may be distributed between the gas turbine engine 10 and a location remote from the gas turbine engine 10. The processor may include at least one microprocessor and may comprise a single core processor, or may comprise multiple processor cores (such as a dual core processor or a quad core processor).

The memory may be located on the gas turbine engine 10, or may be located remote from the gas turbine engine 10, or may be distributed between the gas turbine engine 10 and a location remote from the gas turbine engine 10. The memory may be any suitable non-transitory computer readable storage medium, data storage device or devices, and may comprise a hard disk and/or solid state memory (such as flash memory). The memory may be permanent non-removable memory, or may be removable memory (such as a universal serial bus (USB) flash drive).

The electrodes 368 that are connected to the z-pins of the composite component are connected to the system 370 at the switch module 374. In the present embodiment the electrodes are connected as through-thickness pairs (e.g. electrodes are provided on opposite ends of the component with respect to the longitudinal axis of the z-pins). The system 370 is configured to detect the electrical properties of one or more of the plurality of the z-pins and use the electrical properties to indicate the extent of delamination (if any) a composite component has experienced.

The switch module 374 is configured and operable to select from which electrode pair a signal should be received. The control unit 372 is used to control the electrode pair selected by the switch module.

Once a signal (in this example an electrical signal) has been received from an electrode pair, the measurement unit 376 measures the electrical properties of the signal, e.g. resistance and/or electrical potential. The data acquisition unit 378 is provided to record the electrical properties measured by the measurement unit.

The data analyser then carries out a number of processing operations to indicate the extent and/or location of any delamination of the plies of the tested composite component. The data analyser may:

1) compare the measured resistance and/or potential with respect to reference values for a pristine (e.g. un-delaminated) composite component;

2) compare the measured resistance and/or potential with candidate delamination configurations. For example, the data analyser may use a suitable meta model (e.g. a neural network or a Kalman filter) that predicts the effect of the z-pin progressive pull out and/or shear rupture on the resistance and/or potential measurements for each array pair; and 3) estimate the locations and extents of the delamination both through the thickness and in a plane of the composite component.

The control unit 372 is configured to perform sequential scans across the entire set of electrode pairs. The pairing of electrodes can be adaptively modified during the measurement process in order to tailor the delamination sensing capability to the actual damage configuration in the composite. As such, a feedback and feedforward arrangement is provided between the control unit 372 and the switch module 374, measurement unit 376, and data analyser 380.

Figure 7:
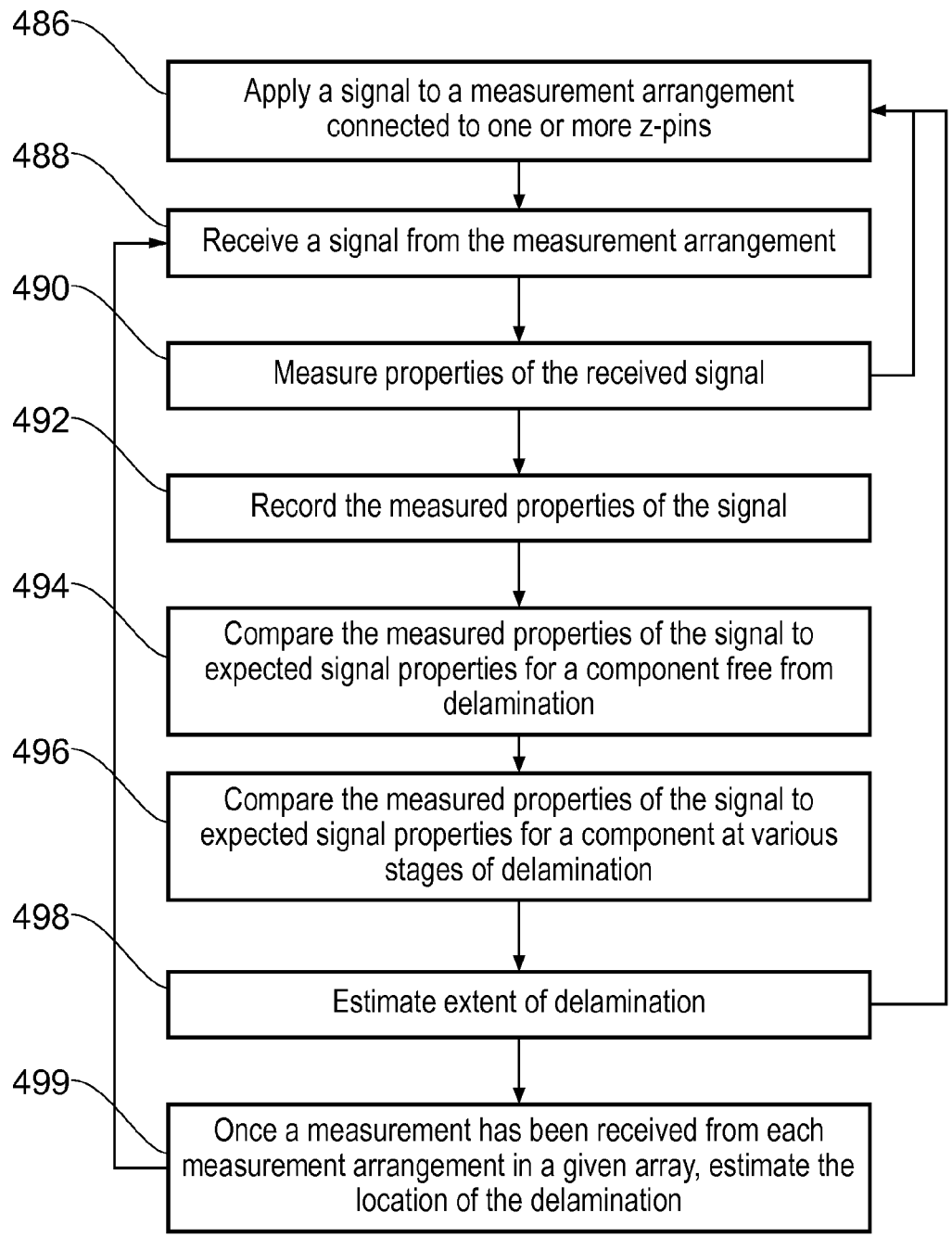
FIG. 7 illustrates a flow diagram of an exemplary method of detecting delamination.

FIG. 7 illustrates a flow diagram of an exemplary method of detecting delamination. Firstly at step 486 the system 370 applies a signal to one or more measurement arrangements, in the present example an electrical signal is applied to one or more pairs of electrodes. At step 488, an electrical signal is received from the pair of electrodes. In step 490, one or more properties (e.g. potential or voltage and/or resistance) of the received electrical signal are measured, e.g. by the measurement unit 376. In step 492, the measured properties of the electrical signal are recorded, e.g. by the data acquisition unit 378. In step 494, the measured properties are compared to the expected signal properties for a component free from delamination and in step 496 the measured properties are compared to the expected signal properties for a component at various stages of delamination. The comparisons may be carried out by the data analyser 380. In FIG. 7 step 494 is shown as being carried out before step 496, but as will be appreciated by the person skilled in the art, step 496 may be performed simultaneously with step 494, before step 494, or step 496 may not be performed if step 494 indicates no delamination has occurred. The next step of the method (step 498) is to estimate the extent of delamination that has occurred based upon the comparisons performed in steps 494 and/or 496. The process is then repeated along a sequence of electrode pairs. In step 499, the measurements and/or comparisons of the electrical signals from all of the electrodes in a given sequence are used to estimate the location of the delamination. As will be appreciated by the person skilled in the art, the method may be modified so that step 498 is performed simultaneously with or after step 499, or step 498 may be performed before step 499 but after signals have been measured and compared for all electrodes in a given array.

Figure 8:
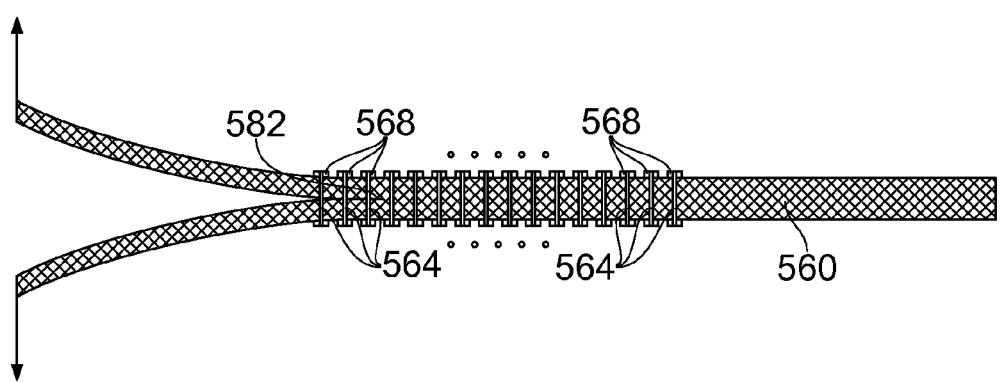
FIG. 8 illustrates a composite component during mode I delamination.

An example of how the system 370 operates will now be explained with reference to FIG. 8. A composite component 560 is arranged as a double cantilever beam and was tested in opening mode I delamination. In this example, the composite component has a length of 145 mm, a width of 20 mm and a thickness of 6 mm. A pre-crack is introduced into the component, the pre-crack having a length of 25 mm. The z-pins 564 of the composite component 560 are carbon z-pins having a 0.28 mm diameter. There are sixteen rows of z-pins and each row comprises five pins connected in parallel. All the pins protrude 1 mm from the external surfaces of the component 560, i.e. from the top and bottom surfaces of the component in the test arrangement. An electrode array 568 is provided and includes sixteen discrete strips on each of the surfaces (top and bottom surfaces) of the component 560. Each of the discrete strips is made of a 1 mm thick silver-epoxy glue. The system 370 is arranged to measure the electrical resistance between each two opposite strips of electrodes in the through-thickness direction. During the test, all sixteen channels of resistances are scanned in sequential order, while the delamination tip 582 propagates from left to right (as shown in FIG. 8) across the z-pin rows that experience progressive pull out. Based upon the measured resistances the system 370 can calculate the extent of the delamination, e.g. the size of the delamination crack at a given point in time.

As will be appreciated by the person skilled in the art, the described embodiments provide a system and a method or detecting and/or locating delamination in a composite component. Such measurements can be used for example to inform when a component needs to be repaired or replaced.

When the composite component is a blade or a casing, the described system may operate to monitor delamination of the blade and/or casing during operation of the gas turbine engine. The invention is particularly suitable for fan blades, e.g. for assessing damage from bird strike.

A benefit of the described embodiments were electrodes are provided on an outer surface of the component is that the composite component does not need to be substantially modified to use the system.

Although the primary purpose of the described system is to detect delamination, the system may also be used to detect the bridging condition that occurs before pin pull out. Further, the system could be configured and/or modified to measure composite deformation.

It will be appreciated by one skilled in the art that, where technical features have been described in association with one or more embodiments, this does not preclude the combination or replacement with features from other embodiments where this is appropriate. Furthermore, equivalent modifications and variations will be apparent to those skilled in the art from this disclosure. Accordingly, the exemplary embodiments of the invention set forth above are considered to be illustrative and not limiting.

The invention claimed is:

1. A method of detecting delamination of a composite component, the composite component having: (i) a plurality of plies, (ii) a plurality of electrodes, and (iii) a plurality of z-pins, where at least one z-pin extends through each of the plurality of plies in the composite component in a direction transverse to the plies, and at least one electrode in the plurality of electrodes being connected to at least one z-pin in the plurality of z-pins, the method comprising:
measuring, with one or more sensors connected to the at least one electrode, one or more material properties of one or more of the z-pins, the one or more z-pins providing through thickness reinforcement of the entire composite component;
comparing the measured material properties to reference material properties of the z-pins; and
estimating whether delamination has occurred based upon the comparison of the measured material properties and the reference material properties.

2. The method according to claim 1, comprising the step of estimating an expected extent of any delamination that has occurred.

3. The method according to claim 1, wherein the method comprises comparing the one or more detected material properties to an expected material property for a composite component without any delamination.

4. The method according to claim 1, wherein the method comprises comparing one or more detected material properties to one or more expected material properties for a composite component at one or more stages of delamination.

5. The method according to claim 1, wherein the method comprises measuring one or more material properties of a plurality of z-pins.

6. The method according to claim 5, comprising estimating the expected location of delamination based upon the comparison of the detected material properties for the z-pins with the reference material properties.

7. The method according to claim 5, wherein the material properties of a plurality of z-pins are measured sequentially.

8. The method according to claim 1, wherein the material properties detected are electrical properties.

9. The method according to claim 1, wherein the z-pins protrude from the composite component and the electrodes are connected to a protruding end of the z-pins.

10. A system for detecting delamination of a composite component including: (i) a plurality of plies, (ii) a plurality of electrodes, and (iii) a plurality of z-pins, where at least one z-pin extends through each of the plurality of plies in the composite component, and at least one electrode in the plurality of electrodes being connected to at least one z-pin in the plurality of z-pins, the system comprising:
   one or more measurement arrangements connected to the at least one electrode, the one or more measurement arrangements being configured to measure material properties of one or more z-pins of the composite component, the one or more z-pins providing through thickness reinforcement of the entire composite component;
   a processor programmed to:
      receive a signal from the one or more measurement arrangements that measures the material properties of the at least one z-pin via the at least one electrode;
      compare data from the received signal to one or more reference parameters of the z-pins; and
      estimate whether delamination of the composite component has occurred based upon the comparison of the data from the received signal to one or more reference parameters of the z-pins.

11. The system according to claim 10, wherein the at least one electrode is in electrical communication with one or more z-pins.

12. An arrangement comprising:
   the system according to claim 10, and
   a composite component, the composite component having a plurality of plies and a plurality of z-pins extending through the composite component in a direction transverse to the plies, and wherein one or more measurement arrangements of the system are connected to one or more z-pins of the composite component.

13. The arrangement according to claim 12, wherein the z-pins protrude from an external surface of the composite component plies.

14. The arrangement according to claim 12, wherein the electrodes include conductive material provided on a surface of the composite component and/or on a surface of a ply of the composite component.

* * * * *